United States Patent
Xu et al.

(10) Patent No.: US 10,349,915 B2
(45) Date of Patent: Jul. 16, 2019

(54) IMAGE PROCESSING APPARATUS, MEDICAL IMAGING DEVICE AND IMAGE PROCESSING METHOD

(71) Applicant: TOSHIBA MEDICAL SYSTEMS CORPORATION, Otawara-shi (JP)

(72) Inventors: Qiqi Xu, Beijing (CN); Xiaojing Wang, Beijing (CN); Li jun Zhang, Beijing (CN); Atsuko Sugiyama, Nasushiobara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 11 days.

(21) Appl. No.: 14/284,970

(22) Filed: May 22, 2014

(65) Prior Publication Data

US 2014/0348401 A1    Nov. 27, 2014

(30) Foreign Application Priority Data

May 22, 2013  (CN) .......................... 2013 1 0192475

(51) Int. Cl.
*A61B 6/00*   (2006.01)
*A61B 6/03*   (2006.01)
(Continued)

(52) U.S. Cl.
CPC ............ *A61B 6/545* (2013.01); *G06F 19/321* (2013.01); *A61B 6/032* (2013.01); *A61B 6/488* (2013.01); *A61B 6/5235* (2013.01); *A61B 8/54* (2013.01)

(58) Field of Classification Search
CPC .................................................... A61B 6/545
See application file for complete search history.

(56) References Cited

U.S. PATENT DOCUMENTS 6,272,469 B1   8/2001   Koritzinsky et al.
6,901,371 B1   5/2005   Koritzinsky et al.
(Continued)

FOREIGN PATENT DOCUMENTS

CN   101123911 A   2/2008
CN   102576387 A   7/2012
(Continued)

OTHER PUBLICATIONS

Office Action dated Nov. 1, 2016 in CN 201310192475.0 with English translation.
(Continued)

*Primary Examiner* — Ping Y Hsieh
*Assistant Examiner* — Jose Torres
(74) *Attorney, Agent, or Firm* — Nixon & Vanderhye P.C.

(57) ABSTRACT

An image processing apparatus according to an embodiment includes a scanning protocol creation unit, an image acquisition unit, a post-processing unit, and a storage unit. The scanning protocol creation unit creates a scanning protocol for a particular part of body of an object. The image acquisition unit acquires source image data by scanning the particular part using an imaging device according to scanning parameters in the scanning protocol. The post-processing unit performs post-processing on the source image data according to post-processing parameters in the scanning protocol to obtain processed image data. The storage unit stores the scanning protocol, or store the source image data and the processed image data or index identifiers thereof in association with parameters related to the scanning protocol as single job data of the object. The scanning protocol includes the scanning and the post-processing parameters, and information related to the imaging device and the post-processing unit.

14 Claims, 6 Drawing Sheets

(51) Int. Cl.
*A61B 8/00* (2006.01)
*G06F 19/00* (2018.01)
*G06K 9/00* (2006.01)

(56) References Cited

U.S. PATENT DOCUMENTS

| | | | |
|---|---|---|---|
| 7,685,262 B2 | 3/2010 | Choubey et al. | |
| 8,280,129 B2 | 10/2012 | Futami et al. | |
| 8,386,273 B2 | 2/2013 | Kaminaga et al. | |
| 2003/0023155 A1* | 1/2003 | Tsunoda | G06F 19/321 600/407 |
| 2003/0045792 A1* | 3/2003 | Heckel | A61B 6/488 600/425 |
| 2003/0139944 A1* | 7/2003 | Carlsen | G06F 19/322 705/2 |
| 2004/0082845 A1 | 4/2004 | Matsumoto et al. | |
| 2005/0267348 A1* | 12/2005 | Wollenweber | A61B 6/032 600/407 |
| 2006/0115135 A1* | 6/2006 | Dehmeshki | G06F 19/321 382/128 |
| 2006/0198499 A1* | 9/2006 | Spies | A61B 6/00 378/207 |
| 2006/0293588 A1* | 12/2006 | Beck | A61B 5/055 600/410 |
| 2007/0109294 A1* | 5/2007 | Gotman | A61B 6/00 345/418 |
| 2007/0127792 A1* | 6/2007 | Virtue | A61B 6/032 382/128 |
| 2007/0238963 A1 | 10/2007 | Kaminaga et al. | |
| 2007/0276214 A1* | 11/2007 | Dachille | G06T 7/0012 600/407 |
| 2008/0119717 A1* | 5/2008 | Profio | G06F 19/327 600/407 |
| 2009/0116710 A1 | 5/2009 | Futami et al. | |
| 2009/0175524 A1* | 7/2009 | Kachi | G01R 33/54 382/131 |
| 2010/0040268 A1* | 2/2010 | Boeing | A61B 6/482 382/128 |
| 2012/0041909 A1* | 2/2012 | Glaser-Seidnitzer | G01R 33/543 706/12 |
| 2012/0213326 A1 | 8/2012 | Walker et al. | |
| 2012/0271840 A1* | 10/2012 | Vosniak | G06F 19/3406 707/758 |
| 2013/0021030 A1* | 1/2013 | Zuehlsdorff | G01R 33/543 324/309 |
| 2014/0098933 A1* | 4/2014 | Profio | A61B 6/03 378/19 |
| 2014/0270053 A1* | 9/2014 | Larson | A61B 6/032 378/4 |
| 2014/0328447 A1* | 11/2014 | Koweek | A61B 6/405 378/4 |

FOREIGN PATENT DOCUMENTS

| | | |
|---|---|---|
| JP | 2004-154560 A | 6/2004 |
| JP | 2007-167634 A | 7/2007 |
| JP | 2009-131614 A | 6/2009 |

OTHER PUBLICATIONS

Japanese office action dated Jan. 23, 2018 in Patent Application No. JP 2014-104702.

Japanese office action dated Jul. 31, 2018 in Patent Application No. JP 2014-104702.

Chinese office action dated Sep. 3, 2018, in Patent Application No. CN 201310192475.0 with English translation.

* cited by examiner

IMAGE PROCESSING APPARATUS, MEDICAL IMAGING DEVICE AND IMAGE PROCESSING METHOD

CROSS-REFERENCE TO RELATED APPLICATIONS

This application is based upon and claims the benefit of priority from Chinese Patent Application No. 201310192475.0, filed on May 22, 2013, the entire contents of which are incorporated herein by reference.

FIELD

The present application relates to the field of image processing and more particularly to an image processing apparatus, a medical imaging device and an image processing method which performs processing on the medical image.

BACKGROUND

In the acquisition and/or processing of a medical image, a great number of parameters may need to be set, for example, parameters including a TR (time of repetition), a TE (time to echo), a FOV (field of view) and the like need to be set when using an MRI (magnetic resonance imaging) system, and parameters including motion correction, distortion correction, an FA (flip angle) threshold, and seed points need to be set during the processing of the acquired image. The setting of these parameters is crucial to the quality of the image finally obtained; moreover, the consistency in settings of the parameters also contributes to enhancing comparability between images.

However, it is a difficult and time-consuming job to optimize these parameters. Therefore, it is desirable to have a mechanism which enables the sharing of parameter settings as well as related data among different devices and different medical institutions. Besides, it is also desirable to track and compare, through the aforementioned mechanism, the images obtained for the same patient at different periods.

BRIEF DESCRIPTION OF THE DRAWINGS

The present invention will be better understood with reference to the following description taken in conjunction with accompanying drawings in which identical or like reference signs designate identical or like components. The accompanying drawings, together with the detailed description below, are incorporated into and form a part of the specification and further serve to illustrate, by way of example, preferred embodiments of the present invention and to explain the principle and advantages of the present invention. In the accompanying drawings.

DETAILED DESCRIPTION

A brief summary of the present invention is given below to provide a basic understanding of some aspects of the present invention. It should be appreciated that the summary, which is not an exhaustive overview of the present invention, is not intended to identify the key or critical parts of the present invention nor limit the scope of the present invention, but merely to present some concepts in a simplified form as a prelude to the more detailed description that is discussed later.

It is an object of the present invention to provide an image processing apparatus, a medical imaging device and an image processing method, which enables data sharing and data comparison and analysis among different devices or medical institutions, by storing the scanning parameters and post-processing parameters when acquiring a medical image.

In accordance with an aspect of the present invention, there is provided an image processing apparatus including: a scanning protocol creation unit configured to create a scanning protocol for a particular part of body of an object to be scanned currently; an image acquisition unit configured to acquire source image data by scanning the particular part of the body of the object using an imaging device according to scanning parameters in the scanning protocol; a post-processing unit configured to perform post-processing on the source image data according to post-processing parameters in the scanning protocol to obtain processed image data; and a storage unit configured to store the scanning protocol, or store the source image data and the processed image data or index identifiers thereof in association with parameters related to the scanning protocol as single job data of the object; wherein the scanning protocol includes the scanning parameters, the post-processing parameters, information related to the imaging device to be used for scanning and information related to the post-processing unit.

In accordance with another aspect of the present invention, a medical imaging device includes the image processing apparatus according to the above aspects of the invention.

In accordance with still another aspect of the present invention, there is provided an image processing method comprising: creating a scanning protocol for a particular part of body of an object to be scanned currently; acquiring source image data by scanning the particular part of the body of the object using an imaging device according to scanning parameters in the scanning protocol; performing post-processing on the source image data according to post-processing parameters in the scanning protocol, to obtain processed image data; and storing the scanning protocol, or storing the source image data and the processed image data or index identifiers thereof in association with parameters related to the scanning protocol as single job data of the object; wherein the scanning protocol includes the scanning parameters, the post-processing parameters, information related to the imaging device to be used for scanning and information related to a post-processing unit.

Further, in accordance with yet another aspect of the present invention, there is provided a computer program for realizing the aforementioned image processing method.

Additionally, in accordance with yet still another aspect of the present invention, there is provided a computer program product in the form of a medium at least readable to a computer, on which computer program codes for realizing the aforementioned image processing method are recorded.

In accordance with the image processing method, image processing apparatus and medical imaging device disclosed herein, data can be conveniently shared as well as compared and analyzed among different medical devices and medical institutions by storing both the scanning parameters and the post-processing parameters of medical images.

Embodiments of the invention are described below with reference to accompanying drawings. The elements and features described in one of the accompanying drawings or embodiments of the present invention may be combined with those shown in one or more other accompanying drawings or embodiments. It should be noted that for the sake of clarity, the representation and description of the components and processing that may be used with the present invention but well known by those skilled in the art are omitted.

Figure 1:
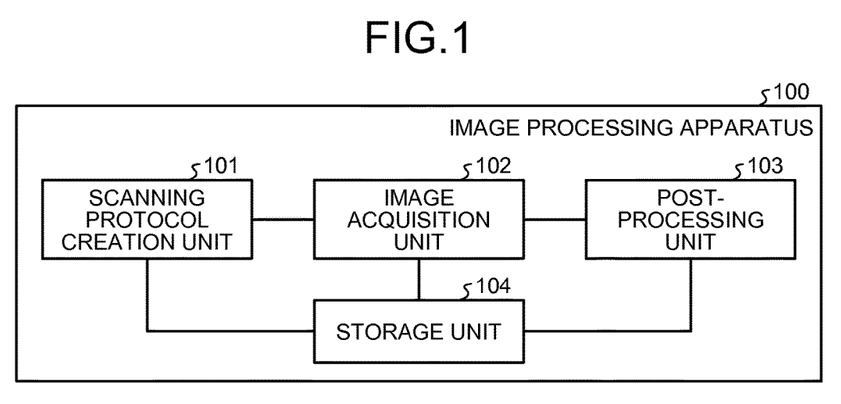
FIG. 1 is a block diagram illustrating the structure of an image processing apparatus according to an embodiment of the present invention.

As shown in FIG. 1, a block diagram illustrating the structure of an image processing apparatus 100 according to an embodiment of the present invention is illustrated. The image processing apparatus 100 includes: a scanning protocol creation unit 101 configured to create a scanning protocol for a particular part of body of an object to be scanned currently; an image acquisition unit 102 configured to acquire source image data by scanning the particular part of the body of the object using an imaging device according to scanning parameters in the scanning protocol; a post-processing unit 103 configured to perform post-processing on the source image data according to post-processing parameters in the scanning protocol to obtain processed image data; and a storage unit 104 configured to store the scanning protocol or store the source image data and the processed image data or index identifiers thereof in association with parameters related to the scanning protocol as single job data of the object, wherein the scanning protocol includes the scanning parameters, the post-processing parameters, information related to the imaging device to be used for scanning and information related to the post-processing unit.

In the present invention, a particular part of the body of the object to be scanned is scanned using a medical imaging device to acquire a desired medical image. The object to be scanned may be, for example, a human being or an animal, and the particular part of the body includes, but is not limited to, a brain, a lung, a heart, a liver, a kidney and other organs or tissues. The medical imaging device here, which may also be referred to as a medical diagnostic device, includes but is not limited to: an X-ray imaging diagnostic device, an ultrasound (UL) diagnostic imaging device, a computed tomography (CT) device, a magnetic resonance imaging (MRI) device, or a positron emission tomography (PET) device or the like.

Generally, various parameters, for example, a scanning speed, intensity of the scanning signal, the slice direction and the number of slices for tomography scanning, need to be set during an imaging (or scanning) process when using these devices. Further, it is also often required to perform corresponding post-processing on the image acquired so as to reflect the condition of the scanned part more accurately and clearly. The post-processing includes various types of image processing performed on an image after reconstruction of the image from data acquired by the scan. However, these operations are complicated, especially the setting of various parameters during the scanning and the post-processing, which requires rich professional knowledge and experience. Therefore, it is desirable to set and optimize the parameters only once and to use the optimized parameters in other imaging processes.

In the present example embodiment, various parameters and related information for scanning and post-processing are defined using a scanning protocol. The scanning protocol creation unit 101 creates a scanning protocol for a particular part of the body of the object to be scanned currently. In an example, the scanning protocol may be deemed to be a data structure which stores the various parameters needed for scanning and post-processing, and records information related to the device which completes the scanning and the post-processing. The form of the scanning protocol may be changed with different body parts, and the particular content of the scanning protocol may be changed with different devices and different individuals. It should be appreciated that the scanning protocol defines what kind of scanning and post-processing are to be performed as well as the way how the scanning and the post-processing will be performed, providing guidance for the operations of the image acquisition unit 102 and the post-processing unit 103.

Taking the MRI scanning of the brain as an example, the scanning parameters may include for example: the number of MPG (motion probing gradient) magnetic fields, a B (diffusion sensitivity coefficient) value, a TR, a TE, a FOV or the like. The post-processing parameters may include, for example, motion correction, distortion correction, a FA threshold, seed points or the like. It should be appreciated that this example is only exemplary and that the present invention is not limited thereto but can be applied to various other medical diagnostic devices as well as various other parts or organs.

After the scanning protocol creation unit 101 creates a scanning protocol for the scanning to be currently performed, the image acquisition unit 102 scans the particular part of the body of the object using an imaging device according to scanning parameters in the scanning protocol, thereby obtaining the source image data. As stated above, the imaging device here may be, but is not limited to a CT or a MRI device.

The post-processing unit 103 performs post-processing on the source image data according to post-processing parameters in the scanning protocol, thereby obtaining processed image data. The processing performed by the post-processing unit may be changed with each part and the property of the acquired source image.

After the aforementioned processing is finished, the storage unit 104 stores the scanning protocol and stores the acquired source image data and processed image data in a database. Wherein, unique index identifiers, through which the storage locations of the source image data and the processed image data can be determined to read the corresponding data, may be assigned to the stored source image data and the processed image data, respectively. Further, the storage unit 104 may further store the source image data and the processed image data in association with parameters related to the scanning protocol as single job data of the object, or stores the above mentioned index identifiers in association with parameters related to the scanning protocol as single job data of the object. Here, the 'job data', which represents the adopted data storage form, may use various existing standards or be defined by the user. In an embodiment, the job data is stored as a DICOM (Digital Imaging and Communications In Medicine) tag, which is a standard for specifying the exchange of medical images and related information thereof. In an embodiment, each patient may have a unique patient identifier, and the job data can be distinguished using a field at least containing the patient identifier. The job data may further include other information such as a timestamp.

As stated above, the scanning protocol may include the scanning parameters, the post-processing parameters, information related to an imaging device to be used for scanning and information related to the post-processing unit. The scanning protocol may be distinguished by, for example, the part scanned and/or the device used. Similarly, the scanning protocol may further include other information such as a timestamp.

In other words, the scanning protocol contains information of the acquisition condition capable of reproducing the obtained source image data and/or the processed image data. For a certain part of a body, there may be one or more optimal scanning protocols, which may be obtained by an experienced medical practitioner from multiple experiments. Through the storage unit 104, the scanning protocols can be stored in various storage mediums and shared among medical practitioners and/or other medical institutions, thereby saving both manpower and material resources.

It can be appreciated that the storage medium mentioned here may be a computer-readable signal medium or a computer-readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic or optical signal, or any suitable combination thereof.

A computer readable signal medium may be any computer readable medium that is not a computer readable storage medium and that can communicate, propagate, or transport a program for use by or in connection with an instruction execution system, apparatus, or device.

As stated above, in this embodiment, the scanning protocol and the job data not only can store the scanning parameters of an image, but also can store the post-processing parameters, and can provide an accurate reference for the following new scanning and post-processing.

Besides, although not shown in FIG. 1, the image processing unit 100 may further include a communication unit and/or a display unit. The communication unit is configured to transmit the scanning protocol and the job data through a wired and/or wireless connection. The display unit is configured to display the scanning protocol and the job data. The communication unit and the display unit, which can be realized using any related technology developed or to be developed, are not directly relevant to the subject matter of the present invention and are therefore not described here in detail.

Figure 2:
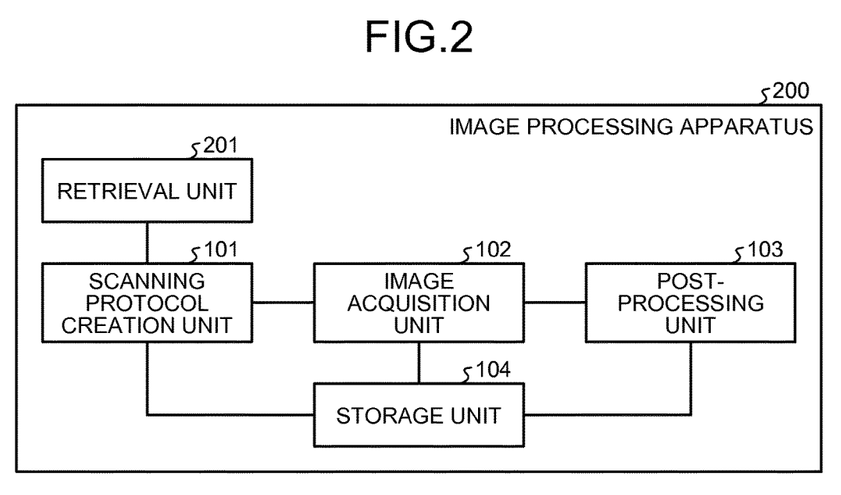
FIG. 2 is a block diagram illustrating the structure of an image processing apparatus according to another embodiment of the present invention.

In accordance with a second embodiment of the present invention, as shown in FIG. 2, in addition to the scanning protocol creation unit 101, the image acquisition unit 102, the post-processing unit 103 and the storage unit 104, an image processing apparatus 200 further comprises a retrieval unit 201.

In an example, the retrieval unit 201 is configured to search for and acquire an existing scanning protocol already stored for the particular part, and the scanning protocol creation unit 101 creates the current scanning protocol according to this existing scanning protocol. In this example, a scanning on a particular part of a patient is required, and the retrieval unit 201 retrieves using, for example, the name of the particular part, to obtain an existing scanning protocol already stored previously. If multiple existing scanning protocols are obtained from the retrieval, any one can be selected according to an optional rule which may be, for example, considering creation times of the scanning protocols.

After the existing scanning protocol is obtained, the scanning protocol creation unit 101 creates the current scanning protocol according to the existing scanning protocol. For example, the scanning protocol creation unit 101 takes the scanning parameters and post-processing parameters in the existing scanning protocol as the scanning parameters and post-processing parameters in the current scanning protocol. Before being used, these parameters can also be modified. For example, device-dependent parameters, if different devices are involved, may be subjected to a corresponding manual or automatic conversion.

The retrieval unit 201 may make a search in a local storage medium or search through a network which may include a local area network, a wide area network or an intranet. The search may be realized using various existing search technologies or engines which are not described here in detail.

In another example, the retrieval unit 201 is configured to search for and acquire existing job data already stored for the particular part of the body of the object to be scanned, and the scanning protocol creation unit 101 creates the current scanning protocol according to the parameters related to the existing scanning protocol in the existing job data.

In this example, the patient to be currently scanned may be subjected to a scanning on the same part previously, and the scanning result was stored in a corresponding database while existing job data of the patient is also stored. It can be appreciated that if the current scanning utilizes exactly the same parameters used in the former scanning and post-processing in the case that the same device and software are used, the workload and time consumed can be minimized while an optimal result can be achieved.

Therefore, the retrieval unit 201 acquires the existing job data, and the scanning protocol creation unit 101 creates the current scanning protocol making use of the parameters in the existing job data which are related to existing scanning protocol. This makes the image data obtained at two consecutive times more comparable as well.

Figure 3:
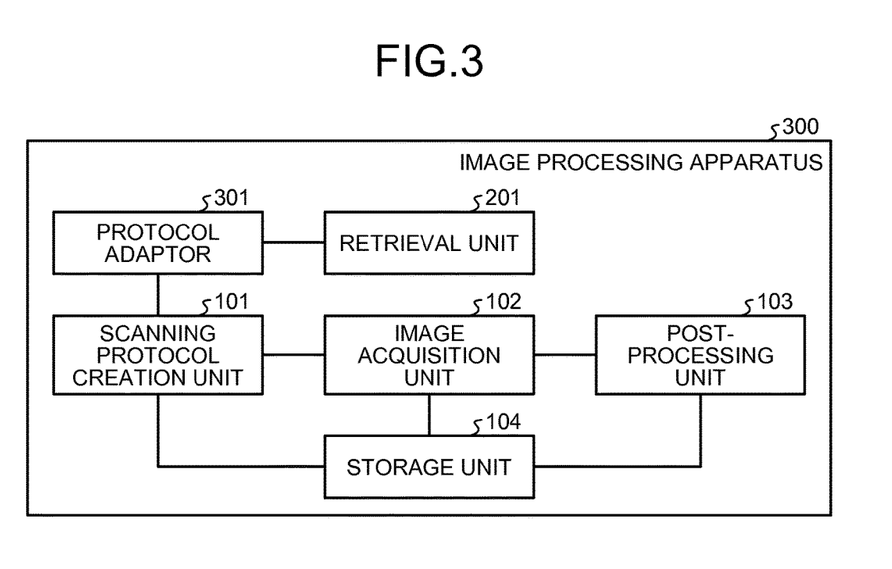
FIG. 3 is a block diagram illustrating the structure of an image processing apparatus according to still another embodiment of the present invention.

Further, FIG. 3 shows a diagram illustrating the structure of an image processing apparatus 300 according to yet another embodiment of the present invention. In addition to each unit shown in FIG. 2, the image processing apparatus 300 further comprises a protocol adaptor 301 configured to adapt the scanning parameters in the current scanning protocol according to the difference between the imaging device for the current scanning and the imaging device corresponding to the existing scanning protocol, and/or to adapt the post-processing parameters in the current scanning protocol according to the difference between the current post-processing unit and the post-processing unit corresponding to the existing scanning protocol.

The protocol adaptor 301 is mainly configured to address the problem that the imaging devices and the version of the components of the post-processing between the operations at two consecutive times are not matched. The adaptation can also be appreciated as conversion, that is, the scanning parameters and/or the post-processing parameters are converted to parameters suitable for the current imaging device and the current post-processing unit. For example, taking MRI as an example, if the MRI systems used at two consecutive times have different gradient system intensities, the protocol adaptor 301 adjusts the related parameters in the existing scanning protocol before using them. The adaptation/conversion can be performed automatically or manually.

In the present embodiment, the protocol adaptor 301 endows the image processing apparatus 300 with compatibility between different versions of hardware and software and the upgradeability can be easily implemented. Further, for many complicated medical imaging devices, even for machine of the same model, the specific settings may be different, and the protocol adaptor 301 may convert such differences into an adjustment on parameters to obtain more accurate processed image data.

Figure 4:
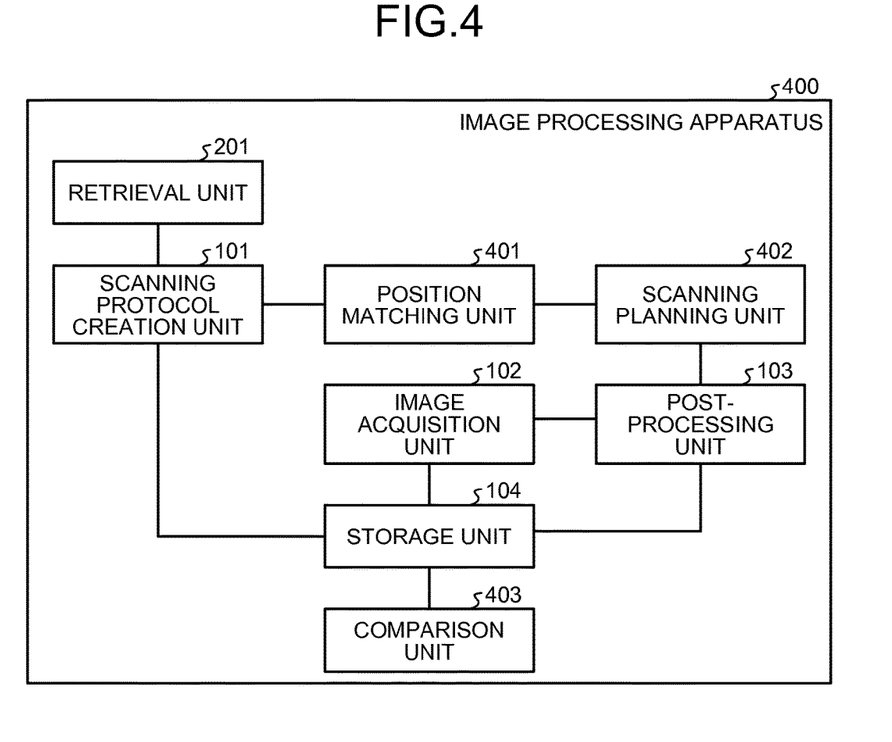
FIG. 4 is a block diagram illustrating the structure of an image processing apparatus according to yet another embodiment of the present invention.

Further, FIG. 4 presents a diagram illustrating the structure of an image processing apparatus 400 according to yet still another embodiment of the present invention. As shown in FIG. 4, in addition to each unit shown in FIG. 2, the image processing apparatus 400 further comprises a position matching unit 401 and a scanning planning unit 402. Further, the image processing apparatus 400 may selectively include a comparison unit 403.

The position matching unit 401 is configured to match the scanned part of the object with the scanned part which corresponds to the source image data corresponding to the existing job data. The scanning planning unit 402 is configured to enable the image acquisition unit 102 to scan according to the scanning parameters in the current scanning protocol and the post-processing unit 103 to perform post-processing according to the post-processing parameters in the current scanning protocol after the position matching unit 401 finishes the matching. The comparison unit 403 is configured to compare the processed image data corresponding to the existing job data with the processed image data currently acquired.

The image processing apparatus 400 may be used to perform tracking, observing and comparatively researching on the same patient. It can be easily appreciated that it requires the same or substantially the same area to be focused upon in the two times of imaging, which can be realized by the position matching unit 401. In an example, the position matching unit 401 includes a pre-scanning module and a registration module. The pre-scanning module is configured to perform pre-scanning on the particular part of the body of the current object to obtain reference volume data, and the registration module is configured to perform registration of the reference volume data with the source image data corresponding to the existing job data. The volume data here refers to the image data representing a certain volume area.

The pre-scanning may be performed relatively roughly and quickly, and the registration module enables the part to be scanned precisely to be found quickly by using the source image data corresponding to the existing job data, and thus, the amount of calculation is greatly decreased, leading to an increase in the scanning speed. The registration can be realized using various existing registration technologies.

After the matching is finished, the scanning planning unit 402 determines a region to be scanned. As the scanning protocol creation unit 101 has created the current scanning protocol, the scanning planning unit 402 starts the scanning and post-processing according to the scanning parameters and post-processing parameters in the current scanning protocol.

If a comparative research is further needed after the scanning and post-processing are finished, the comparison unit 403 can be used to compare the processed image data corresponding to the existing job data with the processed image data obtained currently.

The image processing apparatus 400 may achieve the one-click comparative research. In other words, after a patient identifier is obtained, the scanning protocol can be created and position matching can be performed automatically by searching for the stored job data, and a comparison result is generated finally, which increases the diagnosis efficiency remarkably.

It should be noted that although not shown in FIG. 4, the image processing apparatus 400 may further comprise the protocol adaptor 301 to perform protocol adaptation if appropriate.

It should be appreciated that each embodiment of the present invention can be modified properly to be suitable for various other applications, but is not limited to the aforementioned application.

It is apparent that some processing or methods are also disclosed in the description above on the image processing apparatus according to embodiments of the present invention. Below, the summary of the methods is described without repeating the details which are already discussed above, however, it should be noted that although disclosed in the description of the image processing apparatus, the methods do not certainly employ or are not certainly executed by the aforementioned components. For instance, embodiments of the image processing apparatus may be partially or completely achieved by hardware and/or firmware, and the image processing methods described below may be fully achieved by a computer-executable program, although the image processing methods may employ the hardware and/or firmware of the image processing apparatus.

Figure 5:
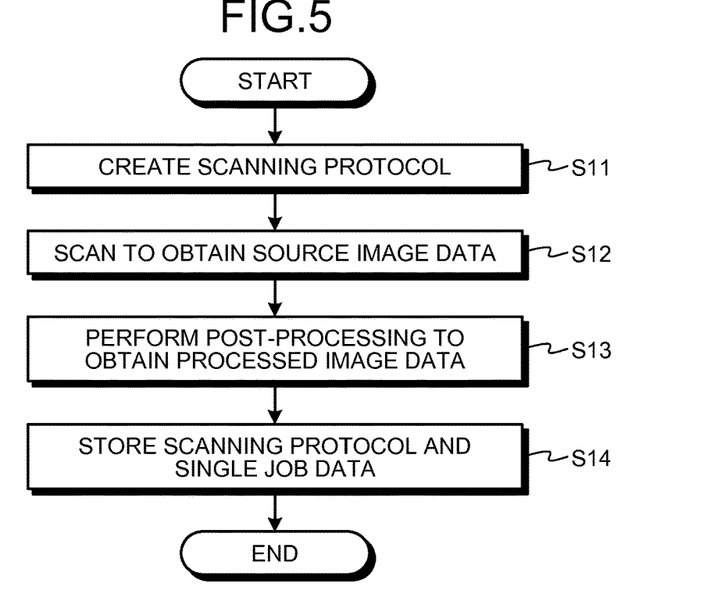
FIG. 5 is a flowchart illustrating the steps of an image processing method according to an embodiment of the present invention.

FIG. 5 is a flowchart of an image processing method according to an embodiment of the present invention. As shown in FIG. 5, the method comprises: creating a scanning protocol for a particular part of body of an object to be scanned currently S11; scanning the particular part of the body of the object using an imaging device according to scanning parameters in the scanning protocol to acquire source image data S12; performing post-processing on the source image data according to post-processing parameters in the scanning protocol to obtain processed image data S13; and storing the scanning protocol, or storing the source image data and the processed image data or index identifiers thereof in association with parameters related to the scanning protocol as single job data of the object S14, wherein the scanning protocol includes scanning parameters, post-processing parameters, information related to the imaging device to be used for scanning and information related to the post-processing. In the method, the scanning parameters and post-processing parameters related to the processed image data are stored.

Although not shown in FIG. 5, the method may further comprise a step of transmitting the scanning protocol and the job data through a wired and/or wireless connection and a step of displaying the scanning protocol and the job data. In an embodiment, the job data is stored as a DICOM tag.

Figure 6:
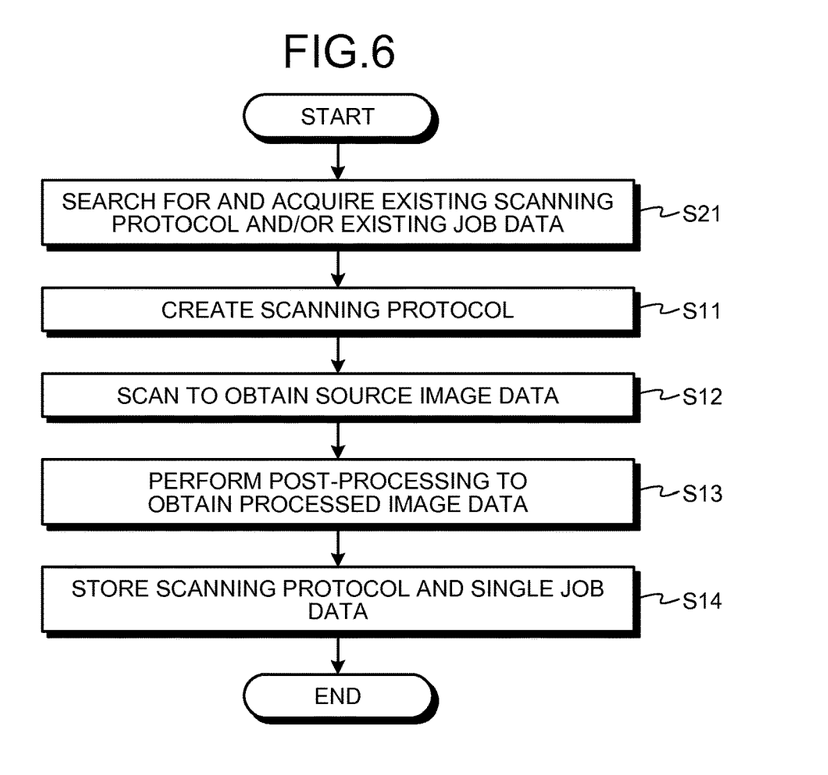
FIG. 6 is a flowchart illustrating the steps of an image processing method according to another embodiment of the present invention.

FIG. 6 shows a flowchart of an image processing method according to another embodiment of the present invention, in addition to Steps S11-S14, the method further includes a retrieval Step S21 prior to Step S11. In an example, existing scanning protocols already stored for the particular part are searched for and acquired and a current scanning protocol is created according to the existing scanning protocols in Step S21. In another example, existing job data already stored for the particular part of the body of the object to be scanned is searched for and acquired and a current scanning protocol is created according to the parameters related to existing scanning protocol in the existing job data in Step S21. The method can define the current scanning and post-processing quickly and accurately making use of the settings of the former scanning and post-processing operations. In an embodiment, a search is made through a network in Step S21.

Figure 7:
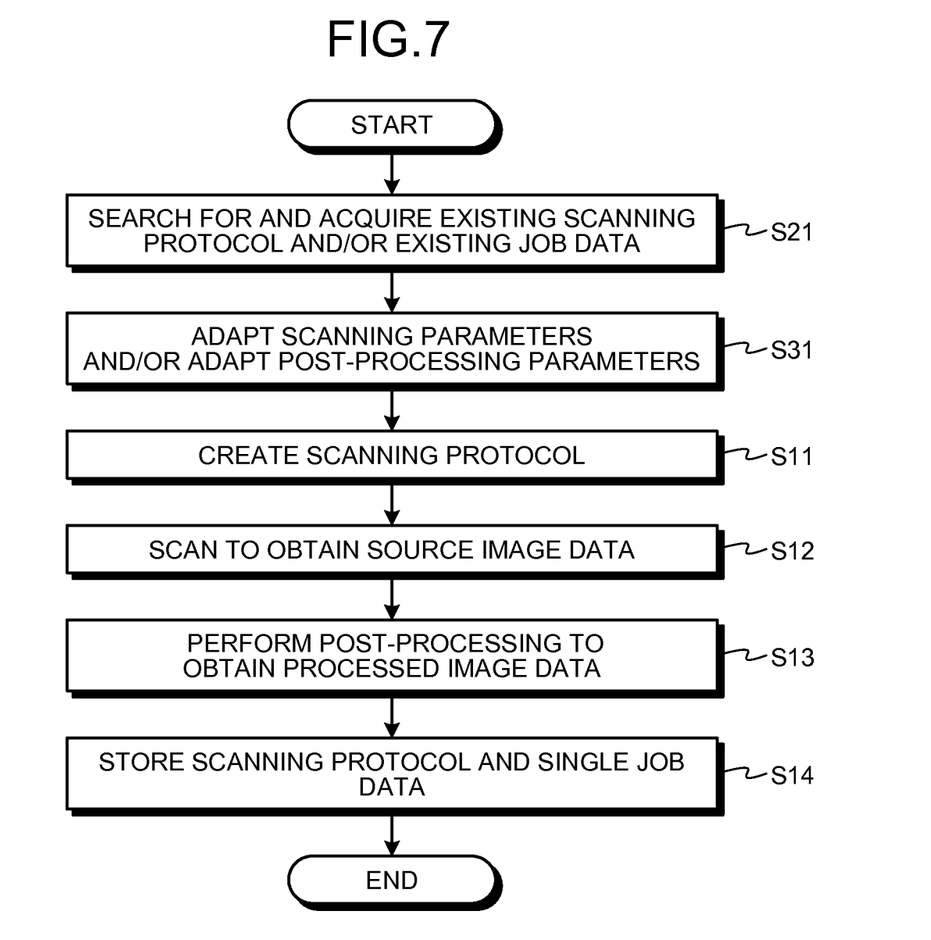
FIG. 7 is a flowchart illustrating the steps of an image processing method according to still another embodiment of the present invention.

In order to address the problems of the inconsistency in hardware and/or versions of software and of upgrading compatibility, the present invention also presents the image processing method shown in FIG. 7. In addition to Steps S11-S14 and Step S21, the method further comprises a Step S31 between steps S21 and S11. In the Step S31, the scanning parameters in the current scanning protocol are adapted according to the difference between the imaging device for the current scanning and the imaging device corresponding to the existing scanning protocol, and/or the post-processing parameters in the current scanning protocol are adapted according to the difference between the current post-processing and the post-processing corresponding to the existing scanning protocol.

Figure 8:
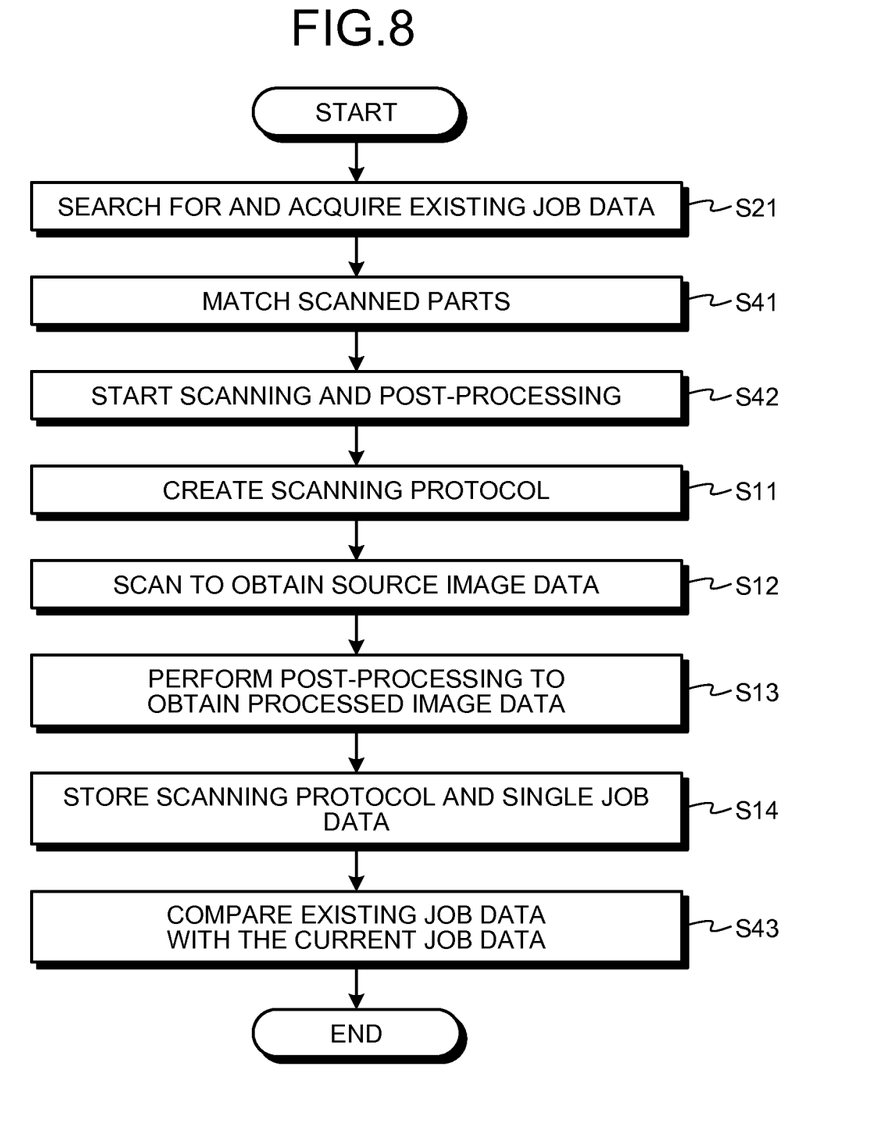
FIG. 8 is a flowchart illustrating the steps of an image processing method according to yet another embodiment of the present invention.

Further, in order to perform tracking and comparatively researching on the same patient, the image processing method shown in FIG. 8 can be used. In addition to Steps S11-S14 and Step S21, the method further comprises steps S41 and S42 as well as an optional Step S43. Wherein the scanned part of the object is matched with the scanned part which corresponds to the source image data corresponding to existing job data in Step S41, and scanning and post-processing are respectively performed according to the scanning parameters and the post-processing parameters in the current scanning protocol in Step S42 after the matching is finished in Step S41. The processed image data corresponding to the existing job data is compared with the currently acquired processed image data in Step S43. Although not shown in FIG. 8, FIG. 8 may further include the Step S31.

In an embodiment, Step S41 may include the following sub-steps: performing pre-scanning on the particular part of the current body of the object to obtain reference volume data; and performing registration of the reference volume data with the source image data corresponding to the existing job data.

More specific details of each step of the image processing method and more possible steps of the image processing method may be referred to the description on each component of the image processing apparatus provided in the above and therefore are not described herein.

Figure 9:
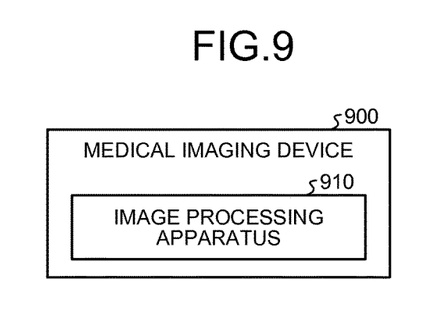
FIG. 9 is a schematic block diagram illustrating a medical imaging device according to an embodiment of the present invention.

FIG. 9 shows a schematic block diagram illustrating a medical imaging device according to an embodiment of the present invention. In order not to obscure the spirit and scope of the present invention, other possible components of the medical imaging device are omitted in FIG. 9. The medical imaging device 900 includes an image processing apparatus 910 for storing the current scanning protocol or job data or creating a current scanning protocol using existing scanning protocol and/or job data to perform scanning and post-processing. The image processing apparatus 910 may be the image processing apparatus 100, 200, 300 or 400 described in any one of the embodiments above. The medical imaging device 900 may be, but not limited to: a X-ray imaging diagnostic device, an ultrasound (UL) diagnostic imaging device, a computer tomography (CT) device, a magnetic resonance imaging (MRI) diagnostic device, a positron emission tomography (PET) device or the like.

The image processing apparatus may be arranged in the medical imaging device in a specific way or manner that is well known to those skilled in the art and is therefore not described in detail herein.

As an example, each step of the aforementioned image processing method and each module and/or unit of the aforementioned image processing apparatus may be implemented as software, firmware, hardware or the combination thereof. In the case where the steps or modules and/or units are realized by software or firmware, a software program for realizing the above mentioned method may be installed in a computer with a dedicated hardware structure (e.g. the general computer 1000 shown in FIG. 10) from a storage medium or network, wherein the computer is capable of implementing various functions when installed with various programs.

Figure 10:
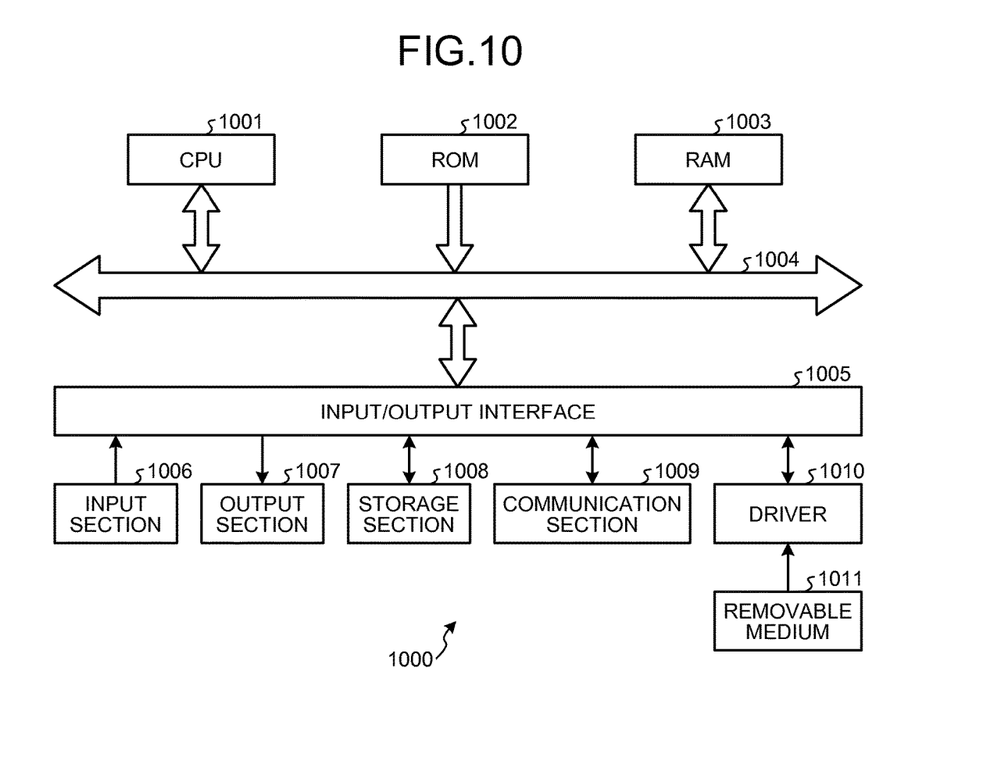
FIG. 10 is an exemplary block diagram illustrating the structure of a computer capable of realizing the embodiments/examples of the present invention.

In FIG. 10, a computing processing unit (namely, CPU) 1001 executes various processing according to a program stored in a read-only memory (ROM) 1002 or a program loaded to a random access memory (RAM) 1003 from a storage section 1008. The data needed for the various processing of the CPU 1001 may be stored in the RAM 1003 as needed. The CPU 1001, the ROM 1002 and the RAM 1003 are linked with each other via a bus 1004. An input/output interface 1005 is also linked to the bus 1004.

The following components are linked to the input/output interface 1005: an input section 1006 (including keyboard, mouse and the like), an output section 1007 (including displays such as cathode ray tube (CRT), a liquid crystal display (LCD), a loudspeaker and the like), a storage section 1008 (including hard disc and the like), and a communication section 1009 (including a network interface card such as a LAN card, modem and the like). The communication section 1009 performs communication processing via a network such as the Internet. A driver 1010 may also be linked to the input/output interface 1005, if needed. If needed, a removable medium 1011, for example, a magnetic disc, an optical disc, a magnetic optical disc, a semiconductor memory and the like, may be installed in the driver 1010 so that the computer program read therefrom is installed in the memory section 1008 as appropriate.

In the case where the foregoing series of processing is achieved through software, programs forming the software are installed from a network such as the Internet or a memory medium such as the removable medium 1011.

It should be appreciated by those skilled in the art that the memory medium is not limited to the removable medium 1011 shown in FIG. 10, which has program stored therein and is distributed separately from the apparatus so as to provide the programs to users. The removable medium 1011 may be, for example, a magnetic disc (including floppy disc (registered trademark)), a compact disc (including compact disc read-only memory (CD-ROM) and digital versatile disc (DVD), a magneto optical disc (including mini disc (MD) (registered trademark)), and a semiconductor memory. Alternatively, the memory medium may be the hard discs included in ROM 1002 and the storage section 1008 in which programs are stored, and can be distributed to users along with the device in which they are incorporated.

The present invention further discloses a program product in which machine-readable instruction codes are stored. The aforementioned image processing methods can be implemented when the instruction codes are read and executed by a machine.

Accordingly, a memory medium for carrying the program product in which machine-readable instruction codes are stored is also covered in the present invention. The memory medium includes but is not limited to soft disc, optical disc, magnetic optical disc, memory card, memory stick and the like.

In the foregoing description on the specific embodiments of the present invention, the features described and/or shown for an embodiment may be used in one or more other embodiments in the same or similar way or combined with those in the other embodiments, or replace those in the other embodiments.

It should be emphasized that the terms 'comprise/include', as used herein, means the existence of a feature, element, step or component in a way not exclusive of the existence or addition of one or more other features, elements, steps or components.

In the aforementioned embodiments and examples, each step and/or unit is represented with a reference sign consisting of figures. It should be understood by those of ordinary skill of the art that the reference signs are merely intended to facilitate description and drawing but are not to be construed as a limitation on an order or any other aspect.

Furthermore, the methods provided in the present invention may be performed sequentially, synchronously or independently in accordance with another time sequences, not limited to the time sequence described herein. Therefore, the implementation orders of the methods described in this specification are not to be construed as a limitation to the scope of the present invention.

Although the present invention has been disclosed with reference to specific embodiments herein, it should be understood that all the embodiments and examples described above are merely illustrative of the present invention but are not to be construed as limiting the present invention. Various modifications, improvements or equivalents can be devised by those skilled in the art without departing from the spirit and scope of the invention, and such modifications, improvements or equivalents should be considered to fall within the scope of the present invention.

What is claimed is:

1. An image processing apparatus, said apparatus comprising:
    at least one computer processor that:
        creates a scanning protocol for a particular part of a body of an object to be scanned, the scanning protocol including scanning parameters, post-processing parameters, information related to an imaging device to be used for scanning and information related to post-processing;
        searches for and acquires existing job data already stored for the particular part;
        matches position of the particular part of the object to be scanned with a position of the particular part which corresponds to existing source-image data corresponding to the existing job data; and
        enables an image acquisition to scan according to the scanning parameters in the scanning protocol and post-processing according to the post-processing parameters in the scanning protocol after finishing the matching of the position of the particular part of the object to be scanned;
        acquires source image data by scanning the particular part of the body of the object using the imaging device according to the scanning parameters in the scanning protocol; and
        performs post-processing on reconstructed source image data according to the post-processing parameters in the scanning protocol to obtain processed image data, the post-processing being performed on the source image data resulting from reconstruction of data acquired by said scanning; and
    a data store that stores the scanning protocol, or stores job data associating the source image data and the processed image data or index identifiers thereof with the scanning parameters and the post-processing parameters.

2. The image processing apparatus according to claim 1, wherein:
    the at least one computer processor further searches for and acquires an existing scanning protocol already stored for the particular part and creates a current scanning protocol according to the existing scanning protocol.

3. The image processing apparatus according to claim 2, wherein:
    the at least one computer processor further adapts the scanning parameters in the current scanning protocol according to a difference between the imaging device for the current scanning and the imaging device corresponding to the existing scanning protocol, and/or adapts post-processing parameters in the current scanning protocol according to a difference between the current post-processing and the post-processing corresponding to the existing scanning protocol.

4. The image processing apparatus according to claim 2, wherein the at least one computer processor searches through a network.

5. The image processing apparatus according to claim 1, wherein:
    the at least one computer processor creates a current scanning protocol making use of the parameters related to existing scanning protocol in the existing job data.

6. The image processing apparatus according to claim 5, wherein:

the at least one computer processor further enables the image acquisition to scan according to the scanning parameters in the current scanning protocol and the post-processing to perform post-processing according to the post-processing parameters in the current scanning protocol respectively after finishing the position matching.

7. The image processing apparatus according to claim 6, wherein:
the at least one computer processor further compares the processed image data corresponding to the existing job data with the processed image data currently acquired.

8. The image processing apparatus according to claim 6, wherein the at least one computer processor:
performs pre-scanning on the particular part of the body of the current object to acquire reference volume data; and
performs registration of the reference volume data with the source image data corresponding to the existing job data.

9. The image processing apparatus according to claim 1, wherein:
the at least one computer processor further transmits the scanning protocol and the job data through a wired and/or wireless connection.

10. The image processing apparatus according to claim 1, wherein:
the at least one computer processor further displays the scanning protocol and the job data.

11. The image processing apparatus according to claim 1, wherein the job data is stored as a DICOM tag.

12. A medical imaging device comprising an image processing apparatus, wherein the image processing apparatus includes:
at least one computer processor that:
creates a scanning protocol for a particular part of a body of an object to be scanned, the scanning protocol including scanning parameters, post-processing parameters, information related to an imaging device to be used for scanning and information related to post-processing;
searches for and acquires existing job data already stored for the particular part;
matches a position of the particular part of the object to be scanned with a position of the particular part which corresponds to existing source image data corresponding to the existing job data;
enables an image acquisition to scan according to the scanning parameters in the scanning protocol and post-processing according to the post-processing parameters in the scanning protocol after finishing the matching of the position of the particular part of the object to be scanned;
acquires source image data by scanning the particular part of the body of the object using the imaging device according to the scanning parameters in the scanning protocol; and
performs post-processing on reconstructed source image data according to the post-processing parameters in the scanning protocol to obtain processed image data, the post-processing being performed on the source image data resulting from reconstruction of data acquired by said scanning; and
a data store that stores the scanning protocol, or stores job data associating the source image data and the processed image data or index identifiers thereof with the scanning parameters and the post-processing parameters.

13. The medical imaging device according to claim 12, wherein the medical imaging device is a computer tomography device or a magnetic resonance imaging device.

14. An image processing method, comprising:
creating a scanning protocol for a particular part of body of an object to be scanned currently, the scanning protocol including scanning parameters, post-processing parameters, information related to an imaging device to be used for scanning and information related to post-processing;
searching for and acquiring existing job data already stored for the particular part;
matching a position of the particular part of the object to be scanned with a position of the particular part which corresponds to existing source image data corresponding to the existing job data;
enabling an image acquisition to scan according to the scanning parameters in the scanning protocol and post-processing according to the post-processing parameters in the scanning protocol after finishing the matching of the position of the particular part of the object to be scanned;
acquiring source image data by scanning the particular part of the body of the object using the imaging device according to scanning parameters in the scanning protocol;
performing post-processing on reconstructed source image data according to the post-processing parameters in the scanning protocol, to obtain processed image data, the post-processing being performed on the source image data resulting from reconstruction of data acquired by said scanning; and
storing the scanning protocol, or storing job data associating the source image data and the processed image data or index identifiers thereof with the scanning parameters and the post-processing parameters.

* * * * *